(12) United States Patent
De Paulis et al.

(10) Patent No.: US 9,844,436 B2
(45) Date of Patent: Dec. 19, 2017

(54) AORTIC VALVE AND CONDUIT GRAFT IMPLANT TOOL

(71) Applicant: Edwards Lifesciences Corporation, Irvine, CA (US)

(72) Inventors: Ruggero De Paulis, Rome (IT); Michael C. Murad, Corona, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 147 days.

(21) Appl. No.: 14/062,424

(22) Filed: Oct. 24, 2013

(65) Prior Publication Data

US 2014/0121764 A1 May 1, 2014

Related U.S. Application Data

(60) Provisional application No. 61/719,275, filed on Oct. 26, 2012.

(51) Int. Cl.
*A61F 2/24* (2006.01)
*A61F 2/06* (2013.01)

(52) U.S. Cl.
CPC ............ *A61F 2/2427* (2013.01); *A61F 2/06* (2013.01); *A61F 2/2496* (2013.01)

(58) Field of Classification Search
CPC ...... A61F 2/2427; A61F 2/243; A61F 2/2436; A61F 2/2466; A61F 2/2496
See application file for complete search history.

(56) References Cited

U.S. PATENT DOCUMENTS

| | | | |
|---|---|---|---|
| 3,997,923 | A | 12/1976 | Possis |
| 4,218,782 | A | 8/1980 | Rygg |
| 4,692,164 | A | 9/1987 | Dzemeshkevich et al. |
| 4,747,848 | A | 5/1988 | Maini |
| 5,123,919 | A | 6/1992 | Sauter et al. |
| 5,139,515 | A | 8/1992 | Robicsek |
| 5,197,979 | A | 3/1993 | Quintero et al. |
| 5,376,112 | A | 12/1994 | Duran |
| 5,545,215 | A | 8/1996 | Duran |

(Continued)

FOREIGN PATENT DOCUMENTS

| | | |
|---|---|---|
| EP | 0169259 A1 | 1/1986 |
| EP | 2478871 A2 | 7/2012 |

(Continued)

*Primary Examiner* — Melanie Tyson
(74) *Attorney, Agent, or Firm* — Guy Cumberbatch; Tom Richardson

(57) ABSTRACT

A sizing tool for use in implanting a composite valved conduit having a prosthetic heart valve on a distal end attached to a conduit graft that extends to a proximal end. The tool includes a proximal handle and a distal shaft, a prosthetic heart valve sizer having an axis affixed to a distal end of the shaft, and a conduit graft replica having an axis mounted on the shaft proximal to the heart valve sizer. A method of securing a composite valved conduit includes introducing to an excised ascending aorta the sizing tool, measuring the aortic annulus with the prosthetic heart valve sizer, and determining whether the coronary arteries have sufficient length or whether an additional tubular coronary extension segment is required to add to one or both of the ends of the coronary arteries by extending the coronary arteries toward the conduit graft replica.

24 Claims, 9 Drawing Sheets

(56) References Cited

U.S. PATENT DOCUMENTS

| | | |
|---|---|---|
| 5,814,096 A | 9/1998 | Lam et al. |
| 5,862,806 A | 1/1999 | Cheung |
| 5,891,195 A | 4/1999 | Klostermeyer et al. |
| 6,001,126 A | 12/1999 | Nguyen-Thien-Nhon |
| 6,090,140 A | 7/2000 | Gabbay |
| 6,264,691 B1 | 7/2001 | Gabbay |
| 6,299,638 B1 | 10/2001 | Sauter |
| 6,352,554 B2 | 3/2002 | De Paulis |
| 6,390,447 B1 | 5/2002 | Mosher |
| 6,482,228 B1 | 11/2002 | Norred |
| 6,783,556 B1 | 8/2004 | Gabbay |
| 6,875,230 B1 | 4/2005 | Morita et al. |
| 6,976,952 B1 | 12/2005 | Maini et al. |
| 7,018,404 B2 | 3/2006 | Holmberg et al. |
| 7,258,698 B2 * | 8/2007 | Lemmon ............... A61F 2/2496 623/2.11 |
| 7,261,732 B2 | 8/2007 | Justino |
| 7,422,603 B2 | 9/2008 | Lane |
| 7,488,346 B2 | 2/2009 | Navia |
| 7,575,592 B2 | 8/2009 | Woo |
| 7,618,447 B2 | 11/2009 | Case et al. |
| 7,625,403 B2 | 12/2009 | Krivoruchko |
| 7,641,686 B2 | 1/2010 | Lashinski et al. |
| 7,641,687 B2 | 1/2010 | Chinn et al. |
| 7,686,844 B2 | 3/2010 | Case et al. |
| 7,717,952 B2 | 5/2010 | Case et al. |
| 7,806,920 B2 | 10/2010 | Duran |
| 7,972,376 B1 | 7/2011 | Dove et al. |
| 2003/0139805 A1 | 7/2003 | Holmberg et al. |
| 2003/0187500 A1 | 10/2003 | Jansen et al. |
| 2004/0193242 A1 | 9/2004 | Lentz et al. |
| 2005/0143810 A1 | 6/2005 | Dauner et al. |
| 2005/0222675 A1 | 10/2005 | Sauter |
| 2005/0267559 A1 | 12/2005 | De Oliveira |
| 2006/0085060 A1 | 4/2006 | Campbell |
| 2006/0167386 A1 | 7/2006 | Drake et al. |
| 2006/0271081 A1 | 11/2006 | Realyvasquez |
| 2007/0156234 A1 * | 7/2007 | Adzich ................. A61F 2/2466 623/2.11 |
| 2008/0147171 A1 | 6/2008 | Ashton et al. |
| 2009/0093873 A1 | 4/2009 | Navia |
| 2009/0157174 A1 * | 6/2009 | Yoganathan .......... A61F 2/2409 623/2.11 |
| 2009/0192604 A1 * | 7/2009 | Gloss .......................... 623/2.11 |
| 2009/0264993 A1 | 10/2009 | Greenan |
| 2010/0274351 A1 | 10/2010 | Rolando et al. |
| 2011/0214398 A1 | 9/2011 | Liburd et al. |
| 2012/0010697 A1 | 1/2012 | Shin et al. |

FOREIGN PATENT DOCUMENTS

| | | |
|---|---|---|
| WO | 03007795 A2 | 1/2003 |
| WO | 2006/013234 A1 | 2/2006 |

* cited by examiner

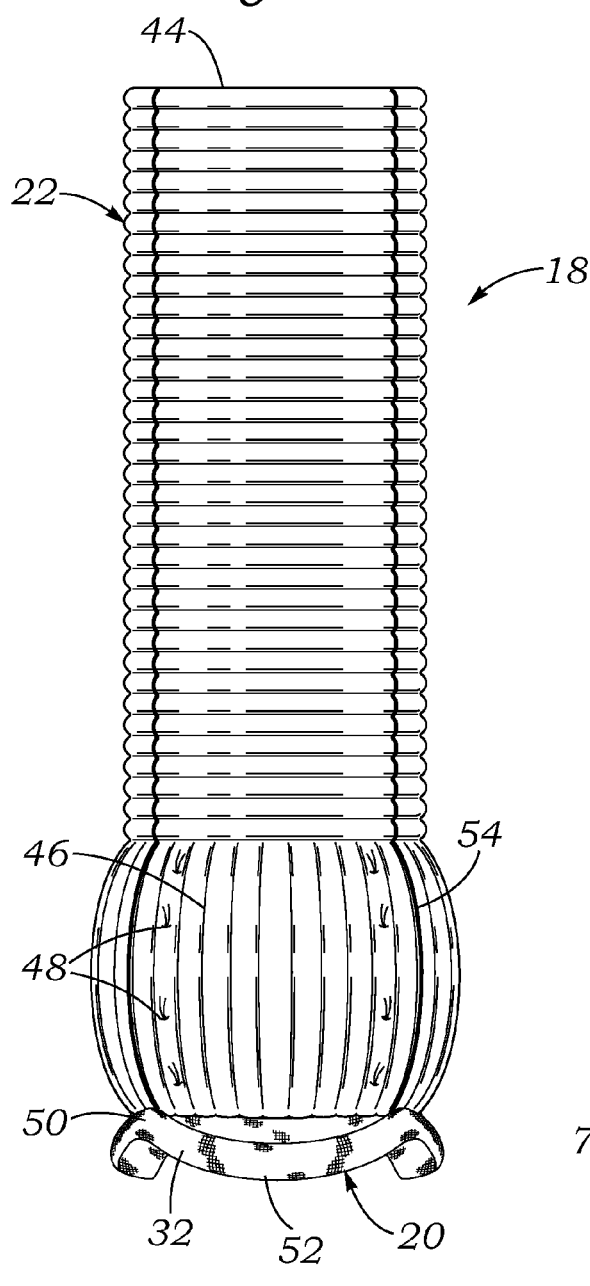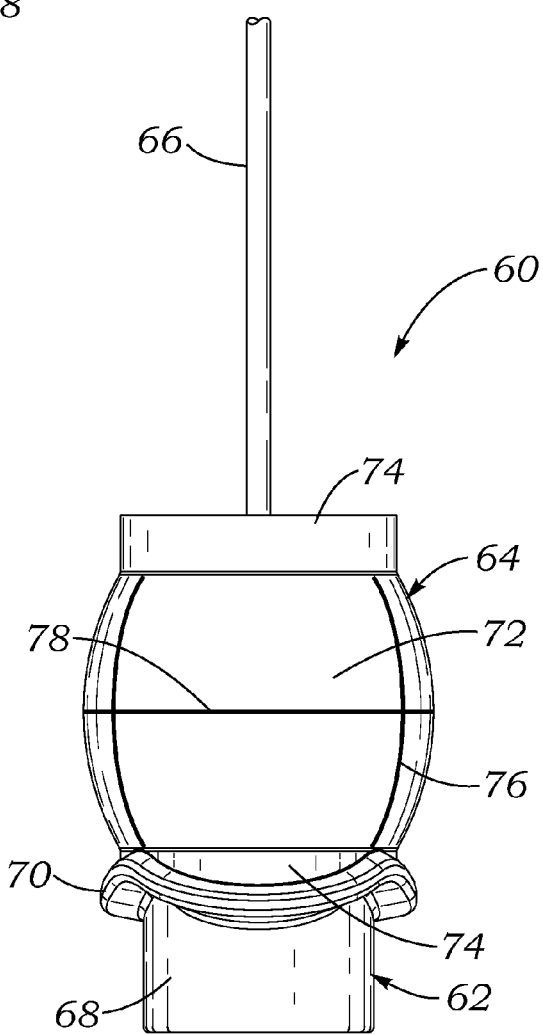

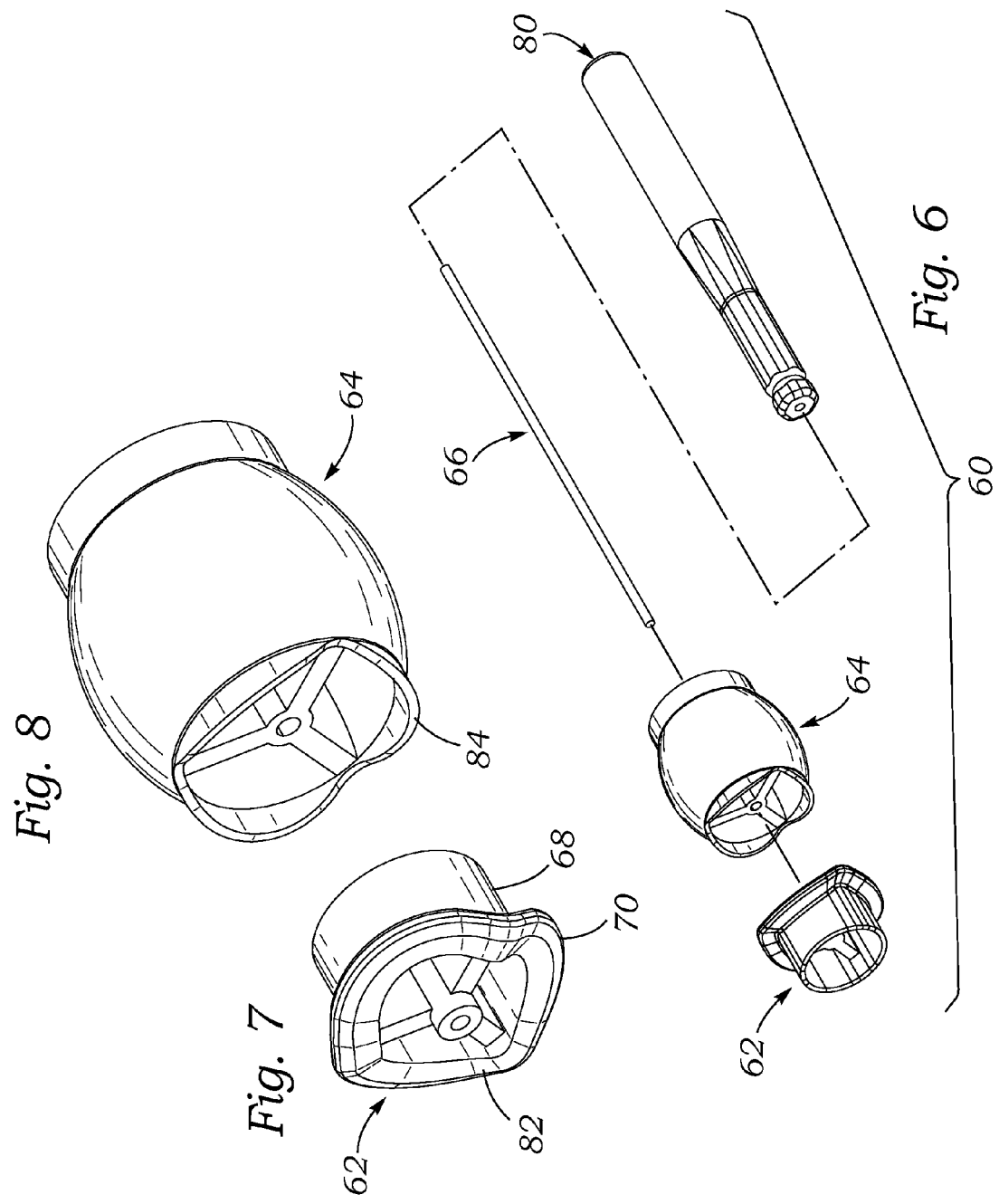

AORTIC VALVE AND CONDUIT GRAFT IMPLANT TOOL

RELATED APPLICATIONS

The present application claims priority under 35 U.S.C. §119 to U.S. Provisional Application Ser. No. 61/719,275, filed Oct. 26, 2012.

FIELD OF THE INVENTION

The present invention relates generally to tools and methods for implanting a prosthetic cardiac implant, in particular a combined aortic valve and conduit graft.

BACKGROUND OF THE INVENTION

Heart valve disease is a widespread condition in which one or more of the valves of the heart fails to function properly. Valve disease can be severely debilitating and even fatal if left untreated. Physicians use a variety of prostheses to correct problems associated with diseased heart valves. A typical procedure involves removal of the native valve and surgical replacement with a prosthetic heart valve.

Aortic and pulmonary heart valves are positioned at the connection of arteries to the left and right heart ventricles, respectively. Replacement or repair of these valves may involve disconnecting and reconnecting the corresponding artery. This process can involve the replacement of a portion of the artery adjacent the valve with a prosthetic conduit graft. Sometimes it is desirable to replace a portion of the artery adjacent the valve due to degeneration of the artery (e.g., aneurysm) even if there is no damage to the valve. On the other hand, the standard surgical approach in patients with ascending aortic aneurysm involving the aortic root and associated aortic valve disease is the replacement of the aortic valve and ascending aorta with a composite valved graft as originally described by Bentall and de Bono in their classical paper (Bentall H. H., De Bono A.: A technique for complete replacement of the ascending aorta, Thorax 1968; 23: 338-9). The ascending aorta adjacent the aortic heart valve connects to coronary arteries that provide aerated blood to the heart muscle, and thus replacement of the ascending aorta involves reconnection of the coronary arteries.

Both the natural aorta and the pulmonary artery have slightly dilated portions adjacent the heart valves called sinuses of Valsalva. The natural sinuses of the aorta are somewhat larger than the sinuses of the pulmonary artery. The aortic sinus portion has three sinuses (bulges) which surround the aortic valve, into two of which open ostia of the coronary arteries. These are called sinuses of Valsalva and are arranged so that the cross-section of the sinus portion has a generally trefoil shape. The diameter and orifice area of the root are greater at the level of the sinus, decrease slightly at the base, but significantly decrease (by 20%) at the level of the sinotubular junction or sinus ridge (where the sinus portion connects to the ascending portion of the aorta which supports the two iliac arteries). The sinotubular junction and the sinuses of Valsalva are considered important to the normal function of the aortic valve. Accordingly, conduit grafts whether valved or not often have lower bulges that simulate the sinuses of Valsalva, though straight tubes without this sinus component are also used.

A number of composite aortic valves and conduit grafts are known in the art, including in U.S. Pat. No. 5,123,919 to Sauter; U.S. Pat. No. 5,139,515 to Robicsek; U.S. Pat. No. 6,352,554 to De Paulis, and others. Vascutek, Ltd. of Inchinnan, Scotland, a division of Terumo of Tokyo, Japan, manufactures several conduit grafts for the ascending aorta, including the BioValsalva porcine aortic biological valved conduit which combines a Triplex Valsalva conduit graft with an Elan porcine stentless biological valve (Koehler, Bellshill, Scotland). The Valsalva conduit graft includes an outwardly-bulged sinus region at its proximal end which mimics the diameter of the natural sinuses. The BioValsalva valved conduit can also be made with Vascutek's Biplex conduit graft which has only two layers—an inner woven polyester and an outer self-sealing elastomer, or with Vascutek's Triplex conduit graft which has three layers—an inner polyester layer, a central self-sealing elastomeric membrane and an outer layer of ePTFE. Another Vascutek graft used is the Gelweave which includes a three layer wall construction of an inner woven polyester, a central elastomeric (gelatin) membrane and an outer ePTFE wrap.

The procedure for implanting an aortic conduit graft, with or without a valve, involves first excising the diseased portion of the ascending aorta, and aortic valve if necessary. The lower end of the conduit graft is then sewn to the valve root above the valve remnant, or the prosthetic aortic valve is sewn to the annulus, and the locations where the coronary arteries meet the sinus region of the conduit graft are marked. Two holes are burned with a cautery device into the side of the conduit graft, and the coronary artery buttons are sewn to the side of the graft at the holes. Typically, at the time of the positioning the combined aortic valve and conduit graft, the surgeon determines whether the coronary arteries have sufficient length to reach the holes made in the conduit graft, and if not, an additional tubular coronary extension segment is added to one or both of the ends of the coronary arteries so that they are not stretched and kinked. Sometimes the native sinuses bulge outward quite far, and the replacement graft is not shaped the same resulting in a gap between the coronary buttons and the side of the graft. This procedure is extremely time-consuming, and thus detrimental to the overall surgery. Finally, the upper end of the conduit graft is anastomosed to the ascending portion of the aorta. The entire process is accomplished while the patient is on cardiopulmonary bypass, and can be fairly time-consuming, especially if the coronaries require lengthening with graft segments.

There is thus a need for devices and methods that reduce the time required to secure a composite aortic valve and conduit graft.

SUMMARY OF THE INVENTION

The present application discloses a sizing tool for use in implanting a composite valved conduit having a prosthetic heart valve on a distal end attached to a conduit graft that extends to a proximal end. The tool includes a proximal handle and a distal shaft, a prosthetic heart valve sizer having an axis affixed to a distal end of the shaft, and a conduit graft replica having an axis mounted on the shaft proximal to the heart valve sizer. The assembly can be made as one piece, with no moving parts, but desirably the graft replica can slide toward the handle along a shaft to create space for utilizing the valve sizer.

By using the sizing tool described herein, the surgeon can simultaneously size the aortic valve while assessing the transposition of the coronary arteries and anastomosis sites, namely whether one or two additional tubular coronary segments will be required. The conduit graft replica simulates the lower portion or sinus region of the conduit graft as it bulges outward during systole and diastole, more so in the latter phase. First, the valve sizer is inserted into the aortic valve to determine the diameter. Once the correctly-sized valve sizer is properly positioned, the surgeon can assess whether the coronary arteries are long enough to reach the conduit graft replica, simulating the sinus region of the conduit graft. If an additional tubular segment will be required because one or both of the coronary arteries are too short to reach the sinus region, the surgeon can prepare for the procedure prior to introducing the actual prosthetic aortic valve conduit, thus saving precious time. The actual procedure involves first sewing the prosthetic aortic valve to the annulus, marking where the coronary arteries (with or without the additional segment) meet the sinus region of the conduit graft, burning two holes in the side of the conduit graft, sewing the coronary artery buttons to the side of the graft, and creating the distal anastomosis.

In accordance with the first embodiment, a tool is provided for use in implanting a composite valved conduit having a prosthetic heart valve on a distal end attached to a conduit graft that extends to a proximal end. The tool includes a proximal handle and a distal shaft, a prosthetic heart valve sizer having an axis affixed to a distal end of the shaft, and a conduit graft replica having an axis mounted on the shaft proximal to the heart valve sizer. The conduit graft replica may be mounted to slide on the shaft, and the tool may include a locking mechanism for fixing the position of the conduit graft replica on the shaft. Preferably, the conduit graft has an elongated tubular proximal section and an outwardly-bulged distal region, and wherein the conduit graft replica has an outwardly-bulged portion that simulates only the outwardly-bulged distal region. The outwardly bulged distal region of the conduit graft replica is desirably axi-symmetric, such as spherical or prolate spherical. The conduit graft replica may also include markers thereon to indicate where on the outwardly-bulged portion the coronary arteries would connect to the outwardly-bulged distal region of the conduit graft. The heart valve sizer may have a cylindrical main body and an outwardly-projecting flange. In one embodiment, the heart valve sizer has a proximal face with an undulating shape around the sizer axis and the conduit graft replica has a distal face that has an undulating shape around the replica axis that mates with the proximal face of the sizer.

In accordance with another embodiment, a tool for use in implanting a composite valved conduit having a prosthetic heart valve on a distal end attached to a conduit graft that extends to a proximal end is disclosed herein. The tool features a prosthetic heart valve sizer having a cylindrical distal portion centered on an axis, and a replica of a portion of a conduit graft having an axis mounted proximal to the heart valve sizer and adapted to be displaced axially toward and away from the heart valve sizer. A locking mechanism is desirably included for fixing the position of the conduit graft replica spaced apart or against from the heart valve sizer. The conduit graft may have an elongated tubular proximal section and an outwardly-bulged distal region, and the conduit graft replica therefore has an outwardly-bulged portion that simulates the outwardly-bulged distal region. The conduit graft replica may also include markers thereon to indicate where on the outwardly-bulged portion the coronary arteries would connect to the outwardly-bulged distal region of the conduit graft. In a preferred about, the heart valve sizer has a proximal face that has an undulating shape around the sizer axis and the conduit graft replica has a distal face that has an undulating shape around the replica axis that mates with the proximal face of the sizer.

Another disclosed embodiment is a tool for use in implanting a composite valved conduit having a prosthetic heart valve on a distal end attached to a conduit graft that extends to a proximal end, the conduit graft having an elongated tubular proximal section and an outwardly-bulged distal region. The tool has a proximal handle and a distal shaft, a prosthetic heart valve sizer having an axis affixed to a distal end of the shaft, and a conduit graft replica having an axis mounted on the shaft proximal to the heart valve sizer and having an outwardly-bulged portion that simulates the outwardly-bulged distal region of the conduit graft. The outwardly-bulged portion of the conduit graft replica further may include markers thereon to indicate where on the outwardly-bulged portion the coronary arteries would connect to the outwardly-bulged distal region of the conduit graft. In one version, the conduit graft replica is mounted to slide on the shaft. The heart valve sizer may have a proximal face that has an undulating shape around the sizer axis and the conduit graft replica has a distal face that has an undulating shape around the replica axis that mates with the proximal face of the sizer. A locking mechanism for fixing the position of the conduit graft replica on the shaft spaced apart from or against the heart valve sizer may be included.

A preferred embodiment of the application comprises a method of securing a composite valved conduit having a prosthetic heart valve on a distal end attached to a conduit graft that extends to a proximal end. The method involves first introducing to an excised ascending aorta a combined sizing tool including a proximal handle and a distal shaft. The tool has a prosthetic heart valve sizer affixed to a distal end of the shaft and a conduit graft replica mounted on the shaft proximal to the heart valve sizer. The aortic annulus is measured with the prosthetic heart valve sizer, and the surgeon determines whether the coronary arteries have sufficient length or whether an additional tubular coronary extension segment is required to add to one or both of the ends of the coronary arteries by extending the coronary arteries toward the conduit graft replica. In a preferred embodiment, the conduit graft replica is mounted to slide on the shaft, and the method further includes proximally displacing the conduit graft replica to separate it from the heart valve sizer during the step of measuring the aortic annulus. The position of the conduit graft replica may be temporarily fixed relative to the shaft after proximally displacing the conduit graft replica. The heart valve sizer may have a proximal face that has an undulating shape around a sizer axis and the conduit graft replica may have a distal face that has an undulating shape around a replica axis that mates with the proximal face of the sizer. Consequently, the method further includes rotating the conduit graft replica to register its distal face with the proximal face of the sizer. Desirably, the conduit graft has an elongated tubular proximal section and an outwardly-bulged distal region, and the conduit graft replica has an outwardly-bulged portion that simulates the outwardly-bulged distal region. Furthermore, the outwardly-bulged portion includes markers thereon to indicate where on the outwardly-bulged portion the coronary arteries would connect to the outwardly-bulged distal region of the conduit graft.

In accordance with another aspect, a method of securing a composite valved conduit having a prosthetic heart valve on a distal end attached to a conduit graft that extends to a proximal end is disclosed herein. A diseased portion of the ascending aorta and native aortic valve is excised, and the aortic annulus measured with a prosthetic heart valve sizer. The surgeon extends the coronary arteries toward a replica of a sinus portion of a conduit graft that is connected to the heart valve sizer to determine whether an additional tubular coronary extension segment is required to add to one or both of the ends of the coronary arteries. If necessary, an additional tubular coronary extension segment is sewn to one or both of the ends of the coronary arteries. Finally, the surgeon implants the composite aortic valve and conduit graft including attaching the coronary arteries with the tubular coronary extension segment(s) to a sinus portion of the conduit graft.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 3 is an elevational view of an exemplary composite valved conduit;

FIG. 4 is an elevational view of the lower part of an exemplary sizing tool for the composite valved conduit of FIG. 3, including a prosthetic heart valve sizer and a conduit graft replica;

FIG. 6 is an exploded perspective view of the exemplary sizing tool of the present application;

FIG. 7 is a perspective view of a proximal end of the heart valve sizer showing an undulating proximal face;

FIG. 8 is a perspective view of a distal end of the conduit graft replica showing an undulating distal face that mates with the proximal face of the heart valve sizer;

DETAILED DESCRIPTION OF THE PREFERRED EMBODIMENTS

Figure 1:
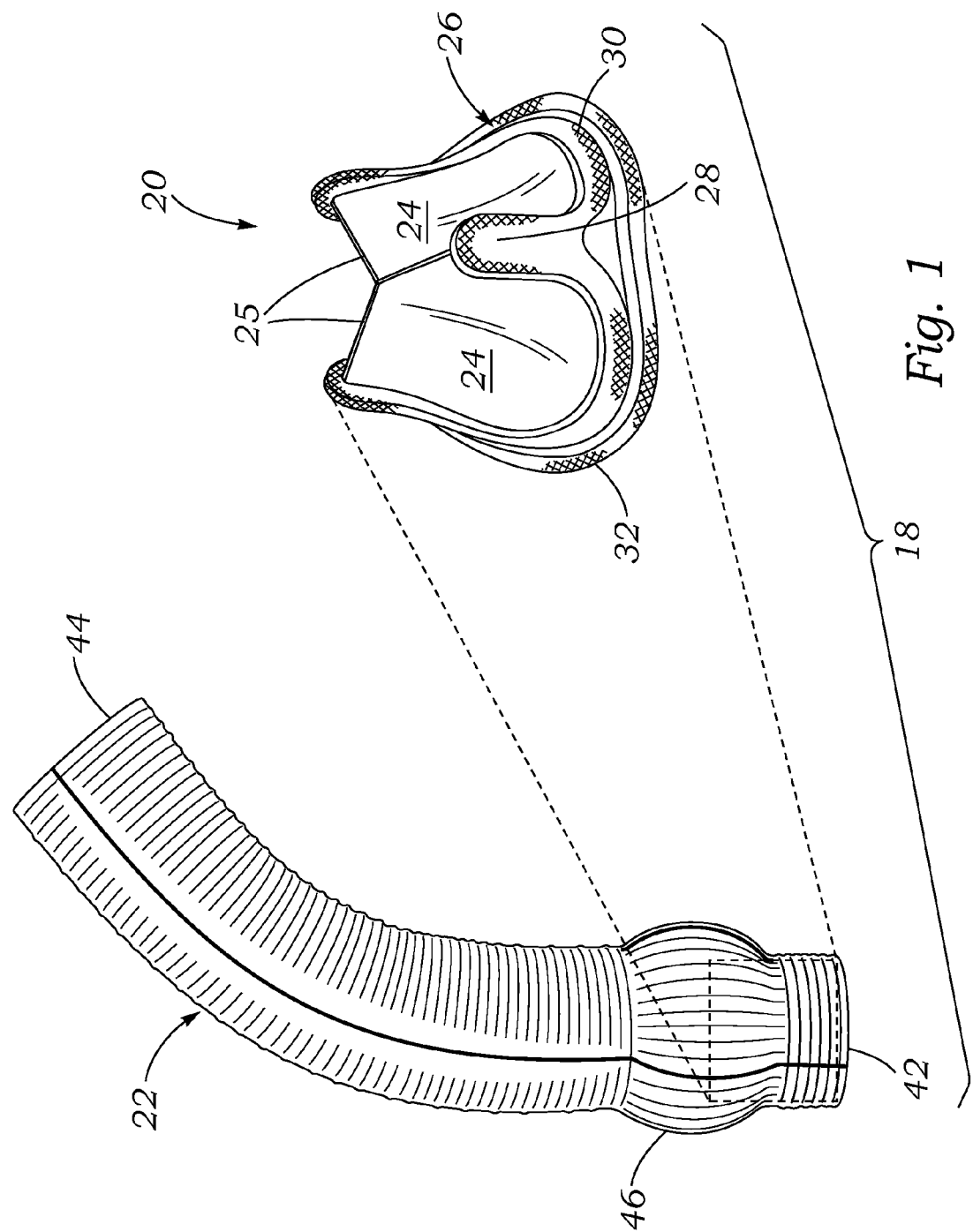
FIG. 1 is a schematic exploded view showing a composite valved conduit including a bioprosthetic heart valve and conduit graft.

FIG. 1 is an exploded view of an exemplary composite valved conduit 18 formed by the combination of a bioprosthetic heart valve 20 coupled to a sealed conduit graft 22. As suggested schematically, the prosthetic heart valve 20 is positioned within one end of the conduit graft 22. Such a valved conduit may be used for replacing a native heart valve and an associated blood vessel in a patient. The aortic valve and the ascending aorta are one non-limiting example of such a valve and an associated blood vessel. The pulmonary valve and the pulmonary artery are another such example.

The heart valve 20 may include a rigid or semi-rigid stent or be a so-called "stentless" type. In the illustrated embodiment, the heart valve 20 comprises a plurality of flexible leaflets 24 (typically three) that are mounted to a peripheral stent structure 26 and form fluid occluding surfaces within the valve orifice to form a one-way valve. The leaflets may be made of various materials, though bioprosthetic tissue such as bovine pericardium is preferred. The stent structure 26 includes a plurality of generally axially extending commissures 28 circumferentially distributed around the valve between and in the same number as the number of leaflets 24. Although not shown, additional components of the heart valve 20 typically include an inner stent and/or wireform support structure that provides a structural skeleton surrounding an inflow orifice and extends up and reinforces the commissures 28. The inner components of the heart valve 20 may be made of suitable metal or plastic.

As is well known, adjacent flexible leaflets 24 connect to and extend upward to meet along each of the commissures 28. In the illustrated embodiment, the structural components of the heart valve 20 support each flexible leaflet 24 along an arcuate valve cusp 30 and along two commissure 28 edges. A free edge 25 of each leaflet 24 extends inward toward a central flow orifice and coapts, or mates, with the free edges of the other leaflets, as shown. The valve orifice is oriented around an axis along an inflow-outflow direction through the valve. The valve commissures 28 project in the outflow direction, with the convex valve cusps 30 extending in the inflow direction between adjacent commissures.

The bioprosthetic heart valves further includes a sewing ring 32 on the inflow end that conforms to the undulating contours of the valve cusps 30, or defines a generally circular, planar ring. The present application should not be considered limited to a particular valve construction unless explicitly stated herein. One particularly useful bioprosthetic valve is selected from the line of Perimount® aortic valves made by Edwards Lifesciences of Irvine, Calif., which includes an undulating sewing ring 32 that generally conforms to the similarly undulating aortic annulus.

The conduit graft 22 is a generally tubular structure that extends from an inflow end 42 to an outflow end 44. In the embodiment shown, the valve 20 is attached within the conduit graft 22 in such a way that the valve leaflets 24 control flow of blood through the conduit graft by permitting blood flow into the conduit inflow end 42 (e.g., blood flow into the aorta, when the conduit is used for aortic replacement) while preventing flow of blood out of the conduit in the opposite direction (i.e., back into the left ventricle of the patient when used for aortic replacement).

The illustrated conduit graft 22 is particularly suited for attachment within the aortic annulus and ascending aorta, and as such closely matches the aortic root anatomy and preferably includes an enlarged region or bulge 46 close to the inflow end 42 that conforms to the sinuses of Valsalva just above the aortic annulus. Alternatively, the bulge 46 is created after implant by the internal pressurization from the blood flow during diastole (and to a lesser extent during systole), when the valve is closed, and that region of the conduit graft 22 is radially expandable, such as providing axial pleats therein. Therefore, the bulge 46 is illustrated for clarity, but it should be understood that the conduit graft 22 could be straight with a relatively more radially flexible portion at the sinus region that creates the bulge 46 after implant. In this respect, the term "outwardly-bulged distal section" of the conduit graft 22 refers to the sinus region that is outwardly bulged at least after implant. Distal and proximal refer to the directions of implant, from the perspective of the surgeon, with the inflow end 42 being distal to the outflow end 44.

In the preferred embodiment, the conduit graft 22 comprises a tubular textile structure, such as Dacron, sealed with a bioresorbable medium. A majority of the conduit graft 22 includes a circumferentially corrugated (i.e., grooved) structure providing longitudinal flexibility and radial compressibility while ensuring that the conduit graft will not unduly radially expand under the pressure of blood flowing therethrough. The conduit graft 22 desirably has a length of from a few centimeters to 10-12 centimeters.

In one embodiment, the conduit graft 22 may be a Vascutek Gelweave gelatin sealed, aortic root graft that is indicated for aortic root replacement using valve sparing or replacement techniques, and available from Vascutek, Ltd. of Inchinnan, Scotland. A bioresorbable medium to provide a temporary seal to the implanted graft is preferred; however, the exemplary bioprosthetic heart valves may also be pre-assembled with other sealed grafts or conduits, such as those that utilize non-bioresorbable material. For instance, the conduit graft 22 can also be Vascutek's Biplex or Triplex conduit grafts. It should be understood that unless excluded by claim language, a variety of sealed conduit grafts are contemplated.

In a preferred embodiment, the exemplary implant includes an Edwards Lifesciences Perimount® aortic valve coupled to the inflow end of a Vascutek Valsalva graft. Either an Edwards Lifesciences GLX-treated, dry-stored Perimount® or a TFX-treated glutaraldehyde-stored Perimount® valve may be used. Vascutek provides its Gelweave, gelatin-sealed graft to be dry stored, or the BiPlex or TriPlex grafts which can be stored in glutaraldehyde.

Figure 2:
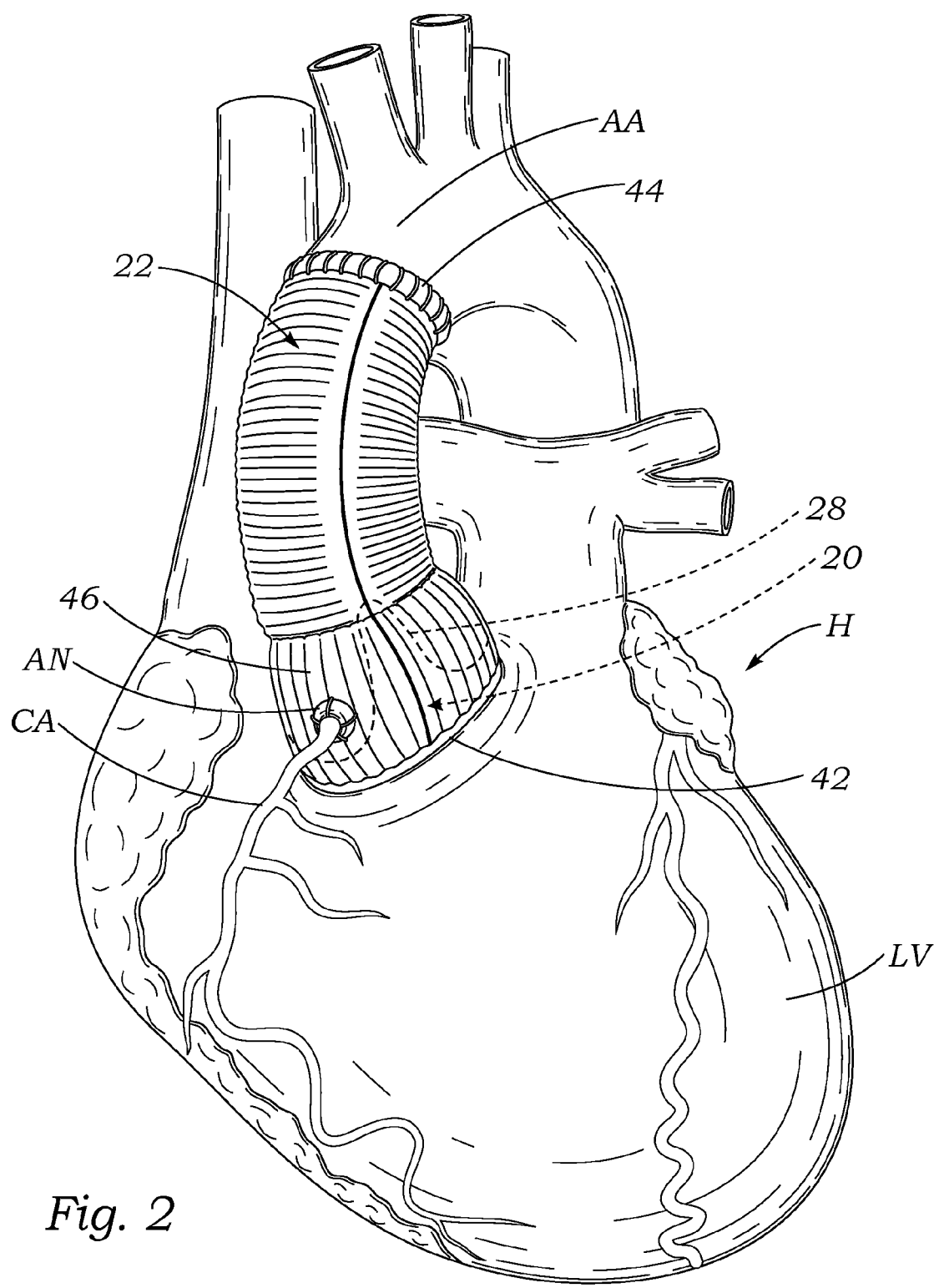
FIG. 2 is an isolated view of a human heart showing implant of a composite valved conduit to replace the aortic valve and a portion of the ascending aorta, including reattachment of the coronary arteries to the side of the conduit graft.

FIG. 2 illustrates a human heart H showing the valved conduit from FIG. 1 implanted above the left ventricle LV to replace the aortic valve and a portion of the ascending aorta AA. The surgeon sews the inflow end 42 to the aortic annulus, and the outflow end 44 to the remainder of the ascending aorta AA. Because the entire valve and a portion of the ascending aorta AA including the sinuses are removed, the two coronary arteries CA (one shown) attach at anastomoses AN to the outwardly-bulged region 46 of the conduit graft 22 where surgically appropriate. That may be between two of the three adjacent pairs of the commissures 28 of the valve 20, but may not be at those locations for both coronaries every time. Again, the bulged region 46 mimics the native sinuses and helps improve blood flow into the coronary arteries CA.

FIG. 3 is an elevational view of the assembled composite valved conduit 18 including the prosthetic heart valve 20 attached within the conduit graft 22. In an exemplary construction, the lower end of the conduit graft 22 is connected to the prosthetic valve 20 above the sewing ring 32. For example, the prosthetic heart valve 20 has a fabric covering to which sutures can be sewn to connect the two components. Stitching 48 can be used to connect the valve commissures (not shown) to the interior of the bulged region 46 of the conduit graft 22. As mentioned, the sewing ring 32 preferably has an undulating contour, with alternating peaks 50 and valleys 52. To assist in the implantation process, relatively dark marker lines 54 are provided on the outside of the conduit graft 22 at the locations of each of the three peaks 50 and extending upward in a proximal direction to the outflow end 44. The surgeon uses these marker lines 54 to rotationally orient the valved conduit 18 relative to the native aortic root. Specifically, the marker lines 54 line up with the native commissures, as do the sewing ring peaks 50 if provided.

A valve sizing tool 60 in FIG. 4 is used to facilitate the placement of the aortic valve and a portion of the aortic conduit including the sinus region. The sizing tool 60 includes a prosthetic valve sizer 62 and a conduit graft replica 64 mounted on a shaft 66. The valve sizer 62 desirably includes a distal cylindrical portion 68 used to measure the orifice diameter through the valve annulus, and a flange 70 used to contact the valve annulus. In the exemplary embodiment, the flange 70 has an undulating contour that mimics the undulating contour of the aortic annulus. More particularly, the flange 70 preferably has a contour identical to the sewing ring 32 of the valved conduit 18, with three peaks and three valleys, as can be seen by comparison between FIGS. 3 and 4. Alternatively, the valve sizer 62 can be a simple cylinder without the flange 70. Indeed, the valve sizer 62 may be selected from a number of conventional sizers, and is made of a relatively hard plastic. Likewise, the graft replica 64 is desirably made of a relatively hard plastic.

In use, the valve sizer 62 simulates the prosthetic aortic valve 20, while the graft replica 64 represents the conduit graft 22. In a preferred embodiment, the graft replica 64 primarily represents the outwardly-bulged region 46 of the conduit graft 22. As illustrated, the graft replica 64 comprises a generally spherical or prolate middle portion 72 with proximal and distal cylindrical sections 74. An axi-symmetric shape such as a sphere or prolate sphere for the bulged portion 72 is considered sufficient to replicate the outwardly-bulged region 46, though other shapes may be used. For example, a straight conduit graft may be simulated by a more cylindrical graft replica, or a three-lobed conduit graft may be simulated by a graft replica having three outward lobes correspond to the three sinuses of the aortic root. As far as absolute sizes, the proximal and distal cylindrical sections 74 as seen in FIG. 4 will typically be about 3-5 mm greater than the corresponding sizer 62 diameter, which in turn approximately matches the native valve orifice diameter. The proportional size of the outwardly-bulged portion 72 relative to the sizer 62 diameter is even larger, and may be obtained from empirical measurements of native sinus-to-valve orifice dimensions, one such study finding that the sinus diameter is about 35% larger than the valve orifice To help orient the graft replica 64 within the aortic root, a series of marker lines 76, 78 may be provided. That is, a series of vertical marker lines 76 correspond to the aortic commissures and line up with the peaks of the undulating flange. In addition, an equatorial marker line 78 helps the surgeon locate the midpoint of the outwardly-bulged region 64 of the conduit graft 22.

Figure 5A:
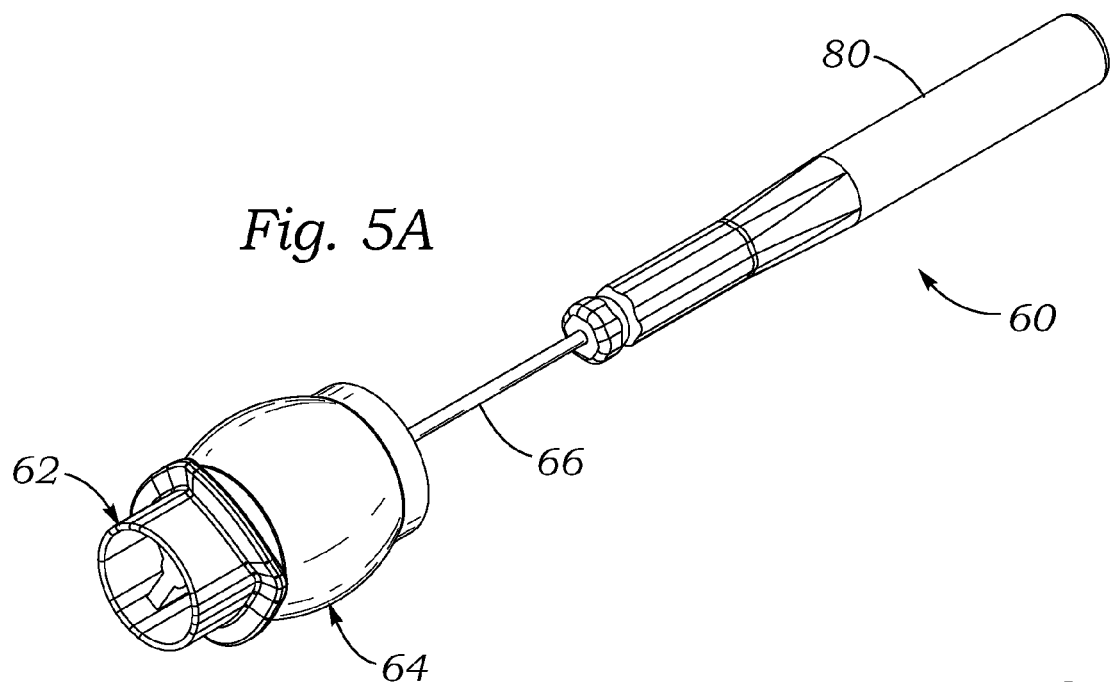
FIGS. 5A and 5B are perspective views of the exemplary sizing tool of the present application showing proximal movement of the conduit graft replica along a central shaft from a position in contact with the heart valve sizer to a position spaced therefrom.
Figure 5B:
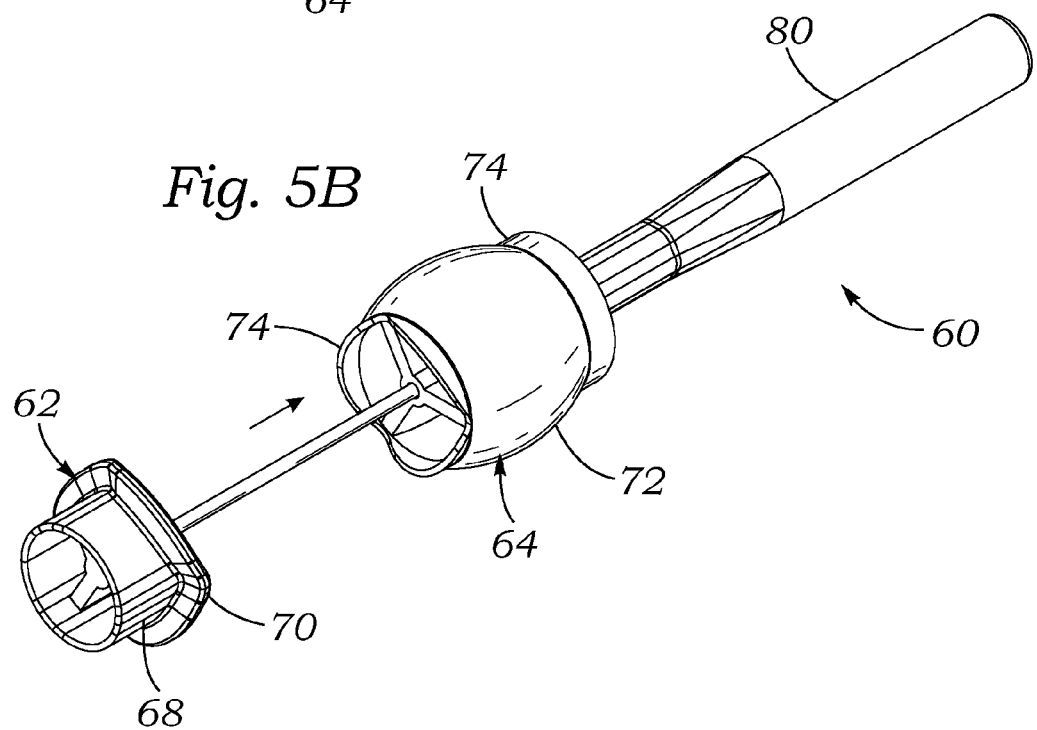

FIGS. 5A and 5B show the exemplary sizing tool 60 of the present application, and proximal movement of the conduit graft replica 64 along the central shaft 66 from a position in contact with the heart valve sizer 62 to a position spaced therefrom. As will be explained below, the sizing tool 60 preferably includes a mechanism for locking the position of the conduit graft replica 64 along the shaft 66, especially at a position spaced from the heart valve sizer 62 adjacent a proximal handle 80.

FIG. 6 is an exploded perspective view of the exemplary sizing tool 60, while FIGS. 7 and 8 show the heart valve sizer 62 and conduit graft replica 64 enlarged. The central shaft 66 preferably fastens to a bore in the distal end of the handle 80 and also within a bore of the heart valve sizer 62, while the conduit graft replica 64 moves axially on the shaft relative to both end components, and is also free to rotate in the illustrated embodiment.

In a preferred version, the heart valve sizer 62 features a contoured proximal face 82 as seen in FIG. 7 that mates with a similarly contoured distal face 84 on the graft replica 64. The mating faces 82, 84 permit rotational alignment of the free-sliding graft replica 64 with the sizer 62, so that the replica is in full contact with the sizer and also perhaps to ensure proper rotational orientation of the replica relative to the sizer and the surrounding annulus. For instance, the flange 70 of the sizer 62 may have an undulating contour as shown that matches up with the native aortic annulus. Consequently, when the sizer 62 seats against the annulus, the peaks of the flange 70 correspond to the native valve commissures. Should the graft replica 64 not be axi-symmetric, such as having three outward lobe bulges, the mating relationship of the faces 82, 84 can be designed so that the graft replica 64 is rotationally oriented with respect to the aortic sinus region, and the outward lobe bulges correspond to the native sinuses. Similarly, if the graft replica 64 has two of three sides specially marked or shaped to facilitate determination of whether the two coronary arteries will reach the eventual graft, the mating relationship of the faces 82, 84 can be designed to ensure those two different sides face the sides where the coronaries are located.

Figure 9:
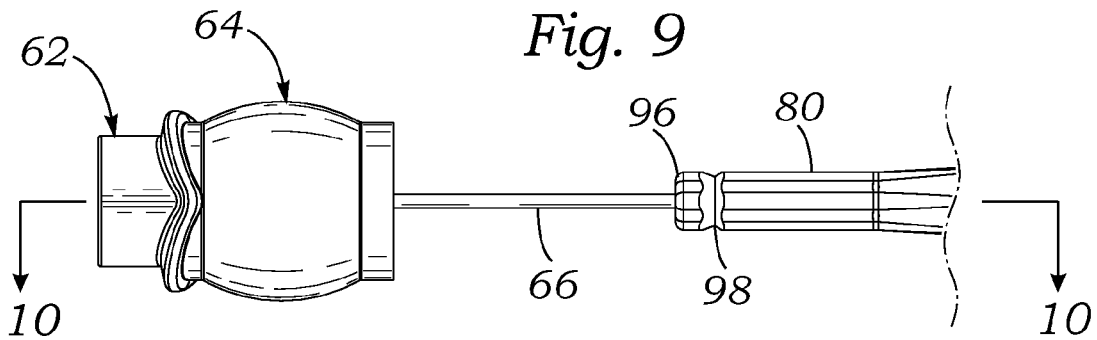
FIG. 9 is a partial view of the exemplary sizing tool.
Figure 10A:
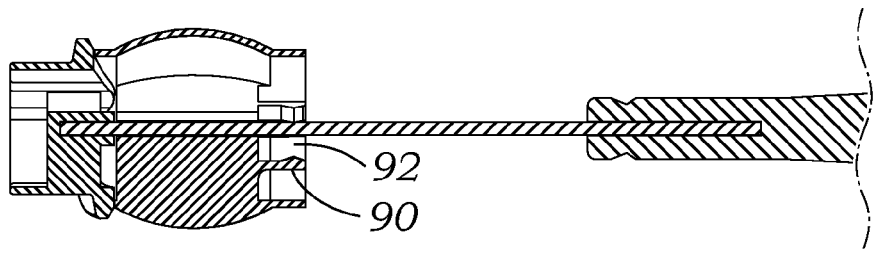
FIGS. 10A-10C are partial longitudinal sectional views through the sizing tool showing proximal movement of the conduit graft replica along the central shaft from a position in contact with the heart valve sizer to a position spaced therefrom and locked to a proximal handle.
Figure 10B:
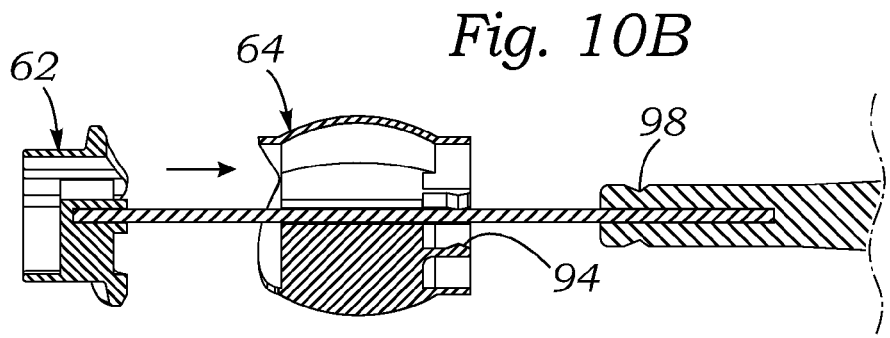
Figure 10C:
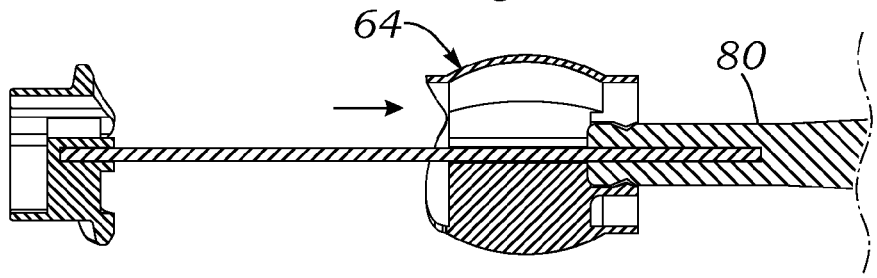

FIG. 9 is a partial elevational view of the exemplary sizing tool 60, and FIGS. 10A-10C are sectional views therethrough. As mentioned, the conduit graft replica 64 moves proximally along the central shaft 66 from a distal position abutting the valve sizer 62, as in FIG. 10A, to a proximal position as in FIG. 10C. An inner hub 90 on the proximal end of the graft replica 64 includes a bore 92 and an inwardly-directed rib 94. The bore 92 closely fits over a distal end 96 of the handle 80, and the hub 90 flexes outward until the rib 94 engages an inward circular groove 98 on the handle, thus temporarily locking the graft replica 64 to the handle 80. Of course this is just one example of a locking mechanism between the graft replica 64 and the handle 80 or shaft 66, and others are contemplated, such as a snap fit, bayonet-style attachment, mating threads, etc. The ability to lock the graft replica 64 in its proximal position enables the surgeon to create space between the graft replica 64 and the valve sizer 62. In this way, contact between the sizer 62 and the valve annulus, and in particular between the undulating flange 70 and the corresponding scalloped annulus, can be clearly observed. After the size of the valve annulus is measured, the surgeon can displace the graft replica 64 distally back to its distal position abutting the valve sizer 62 for a determination of whether an additional tubular coronary extension segment will be required to add to one or both of the ends of the coronary arteries.

Optionally, a similar locking mechanism can also be put on the distal end of the shaft. This would provide resistance against the graft replica 64 moving if the annulus tissue is pushing it up when assessing the coronaries. Otherwise the surgeon might have to manually hold the graft replica 64 down against the valve sizer, which is inconvenient and occupies a hand.

Figure 11A:
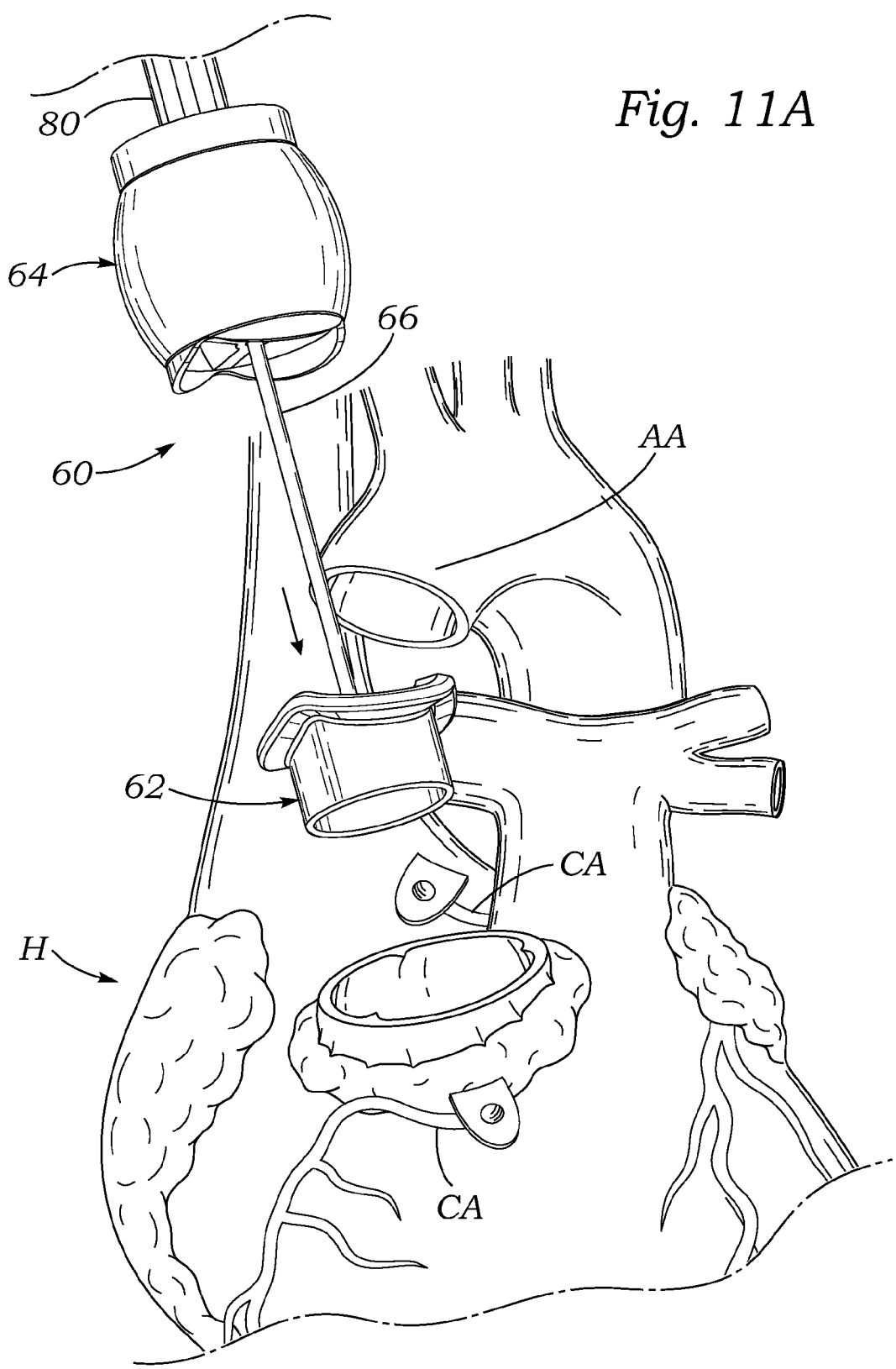
FIGS. 11A-11C show several steps in a method of securing a composite aortic valved conduit to an aortic annulus and ascending aorta, in particular illustrating use of the sizing tool disclosed herein.
Figure 11B:
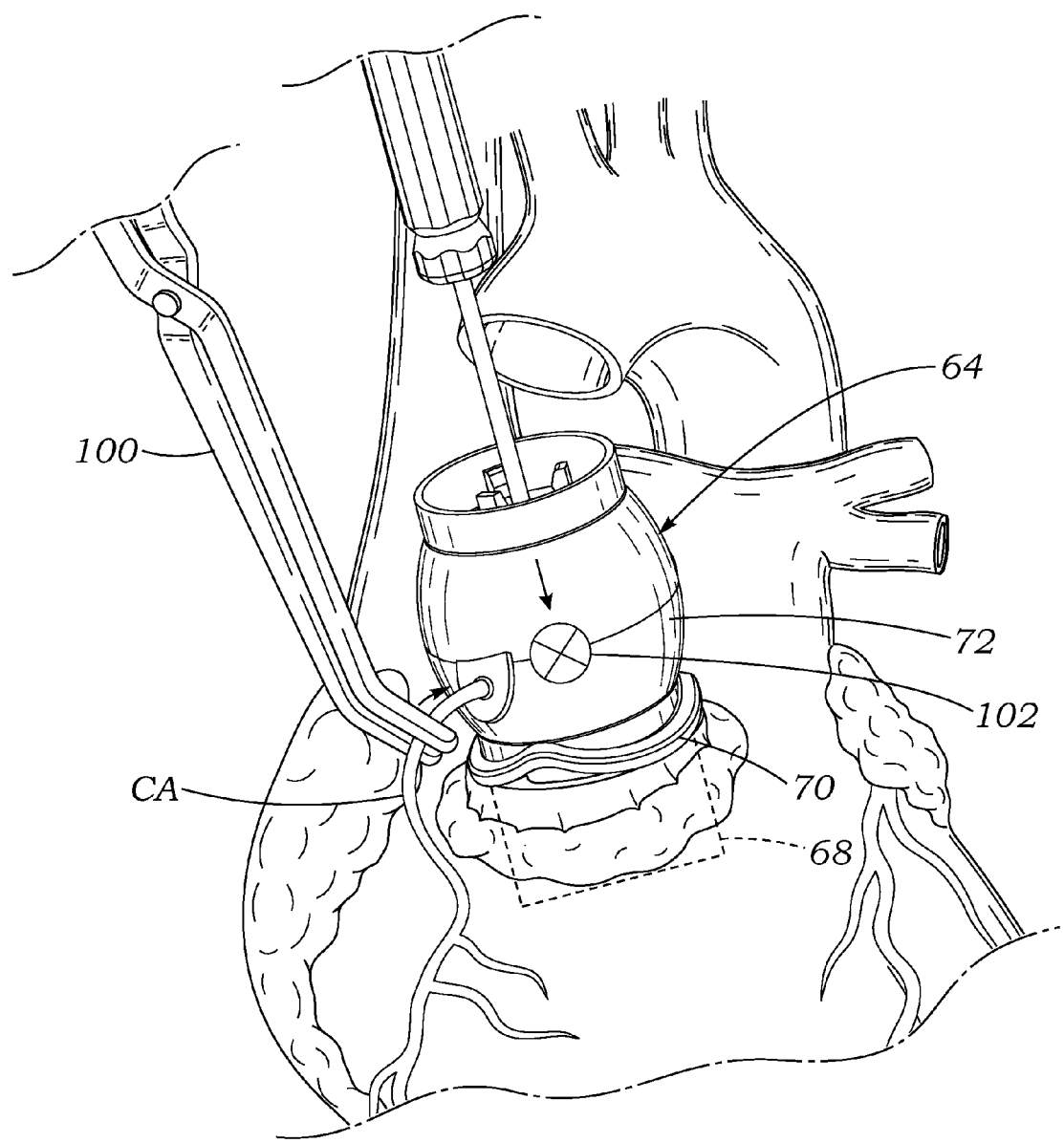
Figure 11C:
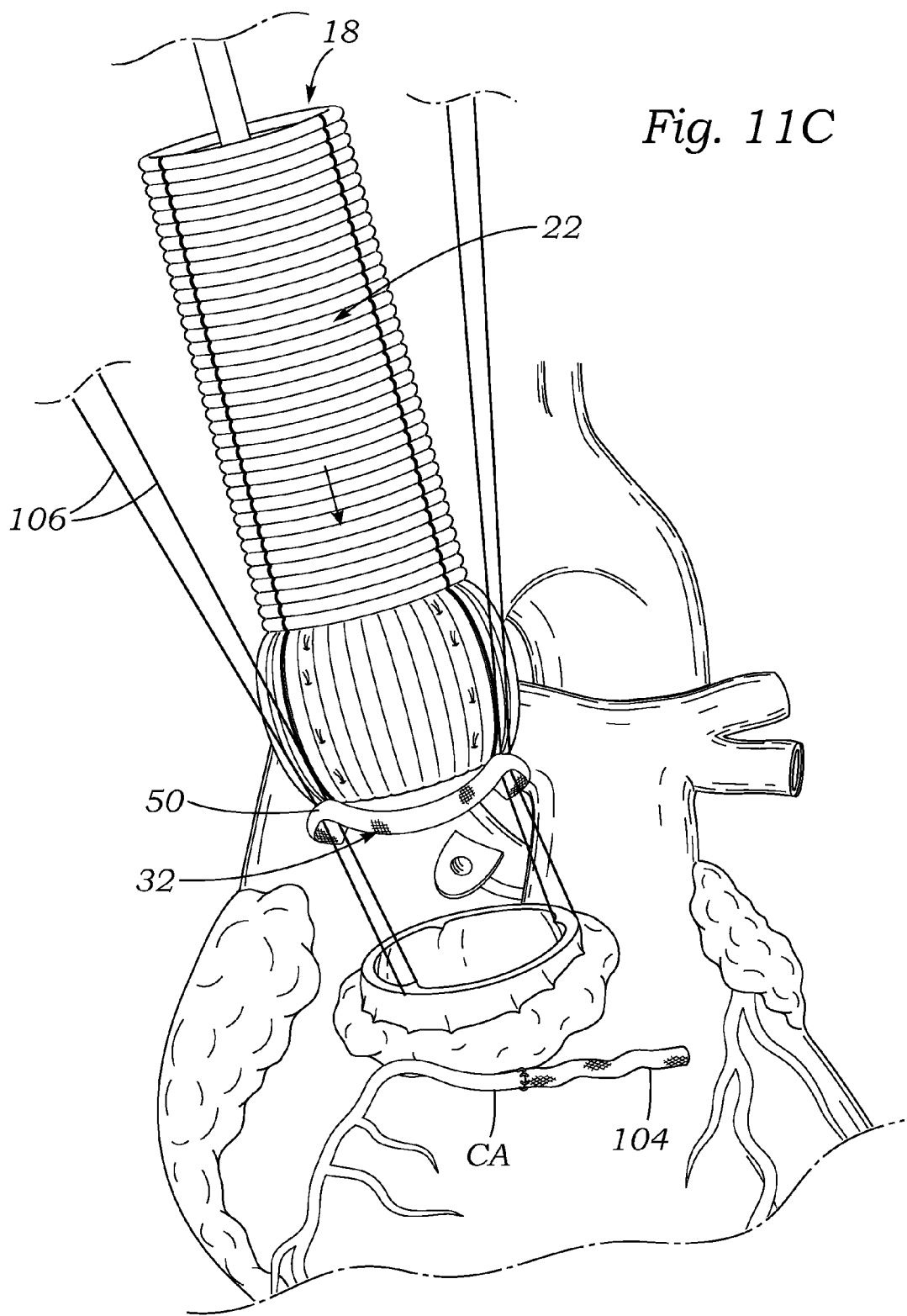

FIGS. 11A-11C show several steps in a method of securing a composite aortic valved conduit to an aortic annulus and ascending aorta, in particular illustrating use of the sizing tool 60 disclosed herein. FIG. 11A shows a portion of the heart H with a section of the ascending aorta AA resected in anticipation of replacing it with a composite valved conduit as described herein. Because the entire valve and a portion of the ascending aorta AA including the sinuses are removed, the two coronary arteries CA are left free, and are typically separated from the respective sinuses along with a small patch or button of tissue, as shown.

FIG. 11A illustrates advancement of the exemplary sizing tool 60 toward the aortic annulus with the conduit graft replica 64 in its proximal position locked to the handle 80, as shown in FIG. 10C. It should be noted at this point that the shaft 66 is preferably a bendable material (e.g., Nitinol) for ease of insertion of the valve sizer 62 toward the aortic annulus.

The surgeon then measures the aortic annulus with the prosthetic heart valve sizer 62, replacing the instrument 60 with a different size if necessary. The cylindrical portion 68 projects into the valve orifice, and the undulating flange 70 contacts the valve annulus, which as noted typically includes an undulating inward ridge. FIG. 11B shows the sizer 62 fully inserted, though the graft replica 64 desirably remains in its proximal position as in FIG. 11A.

After measurement of the annulus, the valve sizer 62 remains in place and the surgeon pushes the conduit graft replica 64 distally along the shaft until it abuts the sizer, into the position shown in FIG. 11B. The graft replica 64 may require rotational orientation in this step to fully mate with the sizer 62, as described above. Subsequently, the surgeon determines whether the coronary arteries CA have sufficient length to meet the conduit graft to be implanted, or whether an additional tubular coronary extension segment is required to add to one or both of the ends of the coronary arteries. This is accomplished by manually grabbing and pulling or extending each of the coronary arteries CA toward the conduit graft replica 64, such as with forceps 100 as shown. In FIG. 11B an alternative target marker 102 is shown on the side of the graft replica 64 simulating one desired location on the graft that is represented by the replica where the coronary artery CA would attach.

If the coronary arteries CA are too short they will not quite reach the bulged region 72 of the graft replica 62, or they may reach the proper location only by stretching and kinking the artery, and the surgeon will recognize that an additional tubular coronary extension segment is required. One or both of the coronary arteries CA may require such an extension.

For example, FIG. 11C shows a tubular graft extension 104 sewn to the visible coronary artery CA, which was deemed too short to reach the desired location on the graft replica 64. By determining whether one or more such tubular coronary extension segments 104 are required at the time of measuring the valve annulus size, the surgeon can ready the extensions and attach them to the coronary arteries CA prior to opening the valved conduit packaging and introducing it to the implant site, thus saving crucial time while the patient is on bypass. Additionally, the implant is not exposed to potential sources of infection prematurely.

FIG. 11C also shows advancement of the composite valved conduit 18 toward the prepared aortic annulus. The procedure for securing the composite valved conduit 18 is similar to that for prosthetic heart valves, and involves pre-installing a plurality of sutures 106 around the annulus and then passing those sutures through corresponding locations around the sewing ring 32. In the illustration, only two such sutures 106 are shown passing through the valve commissures and the peaks 50 of the undulating sewing ring 32, which in turn align with the prosthetic valve commissures. The composite valved conduit 18 is advanced along the array of pre-installed sutures in a so-called parachute delivery, and the individual sutures are tied off or otherwise secured on the proximal side of the sewing ring 32.

Once the distal end of the composite valved conduit 18 is anchored in place, the surgeon forms an aperture in two of the three sinus regions of the conduit graft 22, between the commissure marker lines 54. The apertures are typically formed with a cautery blade to reduce the creation of loose fibers. Then, the free ends of the coronary arteries CA, or tubular graft extensions 104 if added, attach at anastomoses AN to the sinus apertures in the outwardly-bulged region 46 of the conduit graft 22 between two of the three adjacent pairs of the commissures 28 of the valve 20, as seen in FIG. 2. Finally, the proximal end of the conduit graft 22 is anastomosed to the resected ascending aorta to complete the valved conduit implant. Again, a section of the conduit graft 22 may be cut off if it is too long.

To reiterate, the difficulty in placing the aortic valve conduit occurs mainly because of the variability of the positions of the coronary arteries. As stated above, in previous procedures the surgeon determines whether the coronary arteries have sufficient length to reach the lower end of the conduit graft at the time of the positioning the combined aortic valve and conduit graft, and if not, an additional tubular coronary segment is added so that the coronary arteries are not stretched and kinked (the so-called, "Cabrol" technique). This procedure is extremely time-consuming, and thus detrimental to the overall surgery, and exposes the implant to potential sources of infection while the coronaries are lengthened.

By using the valve sizer and graft replica described herein, the surgeon can simultaneously size the aortic valve while assessing the degree of mobilization required for transposition of the coronary arteries and anastomosis sites. In other words, the surgeon can assess whether the additional tubular coronary segment will be required. The conduit graft replica simulates the lower portion or sinus region of the conduit graft as it bulges outward during diastole (and to a lesser extent during systole). First, the valve sizer is inserted into the aortic valve to determine the diameter. Of course, a number of the combined valve sizer and graft replicas will be provided for different sizes. Once the correctly-sized valve sizer is properly positioned, the surgeon can assess whether the coronary arteries are long enough to reach the conduit graft replica, simulating the sinus region of the conduit graft. If an additional tubular segment will be required because one or both of the coronary arteries are too short to reach the sinus region, the surgeon can prepare for the procedure prior to introducing the actual prosthetic aortic valve conduit, thus saving precious time. The actual procedure involves first sewing the prosthetic aortic valve to the annulus, marking where the coronary arteries (with or without the additional segment) meet the sinus region of the conduit graft, burning two holes in the side of the conduit graft, and sewing the coronary artery buttons to the side of the graft.

The graft replica desirably moves axially along a holder shaft to which the valve sizer is attached. In this way, the graft replica can be slid proximally and held away from the valve sizer to facilitate the annulus sizing procedure. Then, once the valve has been sized, the surgeon slides the graft replica down against the valve sizer. Also, the valve sizer preferably includes an outwardly-projecting flange simulating the prosthetic valve sewing ring, which helps axially position the sizer in the annulus to provide a reference platform for the graft replica. Furthermore, the valve sizer preferably has an undulating proximal face which mates with an undulating face on the distal end of the graft replica. This helps ensure that the graft replica is properly axially positioned for the coronary artery measurement.

The graft replica desirably has an axi-symmetric shape which is either spherical or slightly prolate (elongated). Alternatively, the graft replica may have three outward lobes simulating the sinus regions. The mating undulating faces of the valve sizer and graft replica also ensure proper rotational orientation of the graft replica within the aortic root. In one alternative embodiment, marker lines may be provided on the graft replica, such as an axial line at each of the commissure locations, and/or an equatorial line at the midpoint. The marker lines help the surgeon identify the proper placement points for the coronary arteries.

While the invention has been described in its preferred embodiments, it is to be understood that the words which have been used are words of description and not of limitation. Therefore, changes may be made within the appended claims without departing from the true scope of the invention.

What is claimed is:

1. A sizing tool for use in implanting a composite aortic valved conduit having a prosthetic aortic heart valve on a distal end attached to an aortic conduit graft that extends to a proximal end, the aortic conduit graft having an outwardly-bulged distal region adjacent an inflow end and a proximal tubular portion extending to an outflow end coincident with the proximal end of the composite aortic valved conduit, the tool comprising:
   a proximal handle and a shaft extending distally therefrom;
   a prosthetic heart valve sizer having an axis affixed to a distal end of the shaft; and
   an aortic conduit graft replica shaped like the outwardly-bulged distal region of the aortic conduit graft and having an axis mounted on the shaft proximal to the heart valve sizer, wherein the aortic conduit graft replica is mounted to slide on the shaft between the heart valve sizer and the proximal handle.

2. The tool of claim 1, further including a locking mechanism for fixing the position of the aortic conduit graft replica on the shaft.

3. The tool of claim 1, wherein the aortic conduit graft replica has an outwardly-bulged portion that simulates the outwardly-bulged distal region of the aortic conduit graft.

4. The tool of claim 3, wherein the outwardly bulged portion of the aortic conduit graft replica is axi-symmetric.

5. The tool of claim 3, wherein the tool includes markers thereon to indicate where on the outwardly-bulged portion the coronary arteries would connect to the outwardly-bulged distal region of the aortic conduit graft.

6. The tool of claim 1, further including a locking mechanism for selectively fixing the position of the aortic conduit graft replica against the proximal handle or against the heart valve sizer.

7. A sizing tool for use in implanting a composite aortic valved conduit having a prosthetic heart valve on a distal end attached to an aortic conduit graft that extends to a proximal end, the aortic conduit graft having an outwardly-bulged distal region adjacent an inflow end and a proximal tubular portion extending to an outflow end coincident with the proximal end of the composite aortic valved conduit, the tool comprising:
   a proximal handle and a shaft extending distally therefrom;
   a prosthetic heart valve sizer affixed to a distal end of the shaft, the sizer having a cylindrical distal portion centered on an axis; and
   a replica of the outwardly-bulged distal region of the aortic conduit graft having an axis mounted to slide on the shaft and proximal to the heart valve sizer and adapted to be displaced axially along the shaft from a distal position abutting the heart valve sizer to a proximal position adjacent the handle.

8. The tool of claim 7, further including a locking mechanism for fixing the position of the aortic conduit graft replica against the proximal handle.

9. The tool of claim 8, wherein the locking mechanism comprises an inner hub on a proximal end of the aortic conduit graft replica having a bore and an inwardly-directed rib that closely fits over a distal end of the handle having an inward circular groove that engages the rib.

10. The tool of claim 7, wherein the aortic conduit graft replica has an outwardly-bulged portion that simulates the outwardly-bulged distal region of the aortic conduit graft.

11. The tool of claim 10, wherein the tool includes markers thereon to indicate where on the outwardly-bulged portion the coronary arteries would connect to the outwardly-bulged distal region of the aortic conduit graft.

12. The tool of claim 7, wherein the heart valve sizer has a proximal face that has an undulating shape around the sizer axis and the aortic conduit graft replica has a distal face that has an undulating shape around the replica axis that mates with the proximal face of the sizer.

13. A sizing tool for use in implanting a composite aortic valved conduit having a prosthetic heart valve on a distal end attached to an aortic conduit graft that extends to a proximal end, the aortic conduit graft an elongated tubular proximal section and an outwardly-bulged distal region that mimics native aortic sinuses, the tool comprising:
    a proximal handle and a distal shaft extending distally therefrom;
    a prosthetic heart valve sizer having an axis affixed to a distal end of the shaft; and
    an aortic conduit graft replica having an axis mounted on the shaft proximal to the heart valve sizer and having an outwardly-bulged portion that simulates the outwardly-bulged distal region of the aortic conduit graft, wherein the outwardly-bulged portion of the aortic conduit graft replica includes markers thereon to indicate where on the outwardly-bulged portion the coronary arteries would connect to the outwardly-bulged distal region of the aortic conduit graft.

14. The tool of claim 13, wherein the outwardly-bulged portion of the aortic conduit graft replica is axi-symmetric.

15. The tool of claim 13, wherein the aortic conduit graft replica is mounted to slide on the shaft between the heart valve sizer and the proximal handle.

16. The tool of claim 15, wherein the heart valve sizer has a proximal face that has an undulating shape around the sizer axis and the aortic conduit graft replica has a distal face that has an undulating shape around the replica axis that mates with the proximal face of the sizer.

17. The tool of claim 15, further including a locking mechanism for fixing the position of the aortic conduit graft replica on the shaft against the proximal handle.

18. The tool of claim 15, further including a locking mechanism for fixing the position of the aortic conduit graft replica on the shaft against the heart valve sizer.

19. A sizing tool for use in implanting a composite aortic valved conduit having a prosthetic aortic heart valve on a distal end attached to an aortic conduit graft that extends to a proximal end, the aortic conduit graft having an outwardly-bulged distal region adjacent an inflow end and a proximal tubular portion extending to an outflow end coincident with the proximal end of the composite aortic valved conduit, the tool comprising:
    a proximal handle and a shaft extending distally therefrom;
    a prosthetic heart valve sizer having an axis affixed to a distal end of the shaft; and
    an aortic conduit graft replica shaped like the outwardly-bulged distal region of the aortic conduit graft and having an axis mounted on the shaft proximal to the heart valve sizer, wherein the heart valve sizer has a proximal face that has an undulating shape around the sizer axis and the aortic conduit graft replica has a distal face that has an undulating shape around the replica axis that mates with the proximal face of the sizer.

20. The tool of claim 19, wherein the aortic conduit graft replica has an outwardly-bulged portion that simulates the outwardly-bulged distal region of the aortic conduit graft.

21. The tool of claim 20, wherein the tool includes markers thereon to indicate where on the outwardly-bulged portion the coronary arteries would connect to the outwardly-bulged distal region of the aortic conduit graft.

22. The tool of claim 19, wherein the aortic conduit graft replica is mounted to slide on the shaft between the heart valve sizer and the proximal handle.

23. The tool of claim 22, further including a locking mechanism for fixing the position of the aortic conduit graft replica on the shaft against the proximal handle.

24. The tool of claim 23, further including a locking mechanism for fixing the position of the aortic conduit graft replica on the shaft against the heart valve sizer.

* * * * *